United States Patent [19]

Natori

[11] Patent Number: 5,008,371

[45] Date of Patent: Apr. 16, 1991

[54] BIOLOGICALLY ACTIVE POLYPEPTIDE AND USE THEREOF

[75] Inventor: Shunji Natori, Ibaragi, Japan

[73] Assignee: Sanwa Kagaku Kenkyusho Co., Ltd., Aichi, Japan

[21] Appl. No.: 146,892

[22] Filed: Jan. 22, 1988

[30] Foreign Application Priority Data

Jan. 23, 1987 [JP] Japan ................................. 62-14807

[51] Int. Cl.$^5$ ...................... A61K 37/02; C12P 21/02; A01N 37/18
[52] U.S. Cl. .................................. 530/324; 530/858; 435/70.1; 514/2; 514/21
[58] Field of Search .................. 435/70; 530/324, 858; 514/2, 21

[56] References Cited

U.S. PATENT DOCUMENTS 4,355,104 10/1982 Hultmark et al. ..................... 435/70

FOREIGN PATENT DOCUMENTS 59-13730A 1/1984 Japan .
61-122299 6/1986 Japan .

OTHER PUBLICATIONS

Okada et al., "Purification and Characterization of an Antibacterial Protein from Haemolymph of *Sarcophraga peregrina* (Flesh-Fly) Larvae", Biochem. J., vol. 211, pp. 727–734, 1983.
Okada et al., "Primary Structure of Sarcotoxin I, an Antibacterial Protein Induced in the Hemolymph of *Sarcophaga peregrina* (Flesh Fly) Larvae", J. Biol. Chem., vol. 260, pp. 7174–7177, 1985.
Lehrer et al., "Direct Inactivation of Viruses by MCP-1 and MCP-2, Natural Peptide Antibiotics from Rabbit Leukocytes", J. of Virology, vol. 54, 467–472, 1985.
Komano et al., "Purification of Sarcophage (Flesh Fly) Lectin and Detection of Sarcotoxins in the Culture Medium of NIH-Sape-4, an Embryonic Cell Line of *Sarcophaga peregnina*", Biochem. J. (1987), 248, 217–222.
"Eur. J. Biochem", vol. 106, p. 7 (1980).

*Primary Examiner*—Charles F. Warren
*Assistant Examiner*—Christopher Low
*Attorney, Agent, or Firm*—Armstrong, Nikaido, Marmelstein, Kubovcik & Murray

[57] ABSTRACT

A biologically active polypeptide, method of obtaining same and use thereof are disclosed. The polypeptide is obtained through steps of cultivating a cell line established from *Sarcophaga peregrina* embryo to produce the same in a culture medium, as product of the cell line, isolating and purifying the same. The polypeptide shows an anti-virus activity.

2 Claims, 4 Drawing Sheets

BIOLOGICALLY ACTIVE POLYPEPTIDE AND USE THEREOF

BACKGROUND OF THE INVENTION

1. Field of the Invention

The present invention relates to a novel biologically active polypeptide, method of obtaining same as well as use thereof. The polypeptide is obtained through a cultivation of an insect cell and more particularly a cell line established from flesh fly (Sarcophaga peregrina) embryo.

2. Related Arts

It has been known that a certain antibacterial substance will appear in a body fluid, when a vaccine is inoculated to an invertebrate such as insecta ["Eur. J. Biochem." Vol. 106, page 7 (1980)].

The present inventor has also found such a fact on the Sarcophaga peregrina that a certain antibacterial polypeptide appears in its body fluid, when a larva of the insect is injured in its body, the polypeptide being separated and purified to investigate its physicochemical properties [see Jap. Pat. Nos. 59-13730 (A) published Jan. 24, 1984 and 61-122299 (A) published Jun. 10, 1986].

Since the polypeptide produced by the insect shows a wide antibacterial spectrum, almost no toxicity and is a protein, the substance has been expected to be an edible antibiotic but has difficulties in its production, including difficulties relating to obtaining the raw material (the insect per se), isolation and purification thereof.

SUMMARY OF THE INVENTION

A basic object of the invention, therefore, lies in providing a method of obtaining a biologically active polypeptide in a reasonable cost to allow an application thereof for industrial production.

According to the invention, the basic object can be attained by a method which comprises steps of cultivating a cell line established from Sarcophaga peregrina embryo, subjecting a resulting culture medium to an ion-exchange chromatography, a thermal treatment and a gel filtration chromatography to collect a biologically active polypeptide through a separation and fractioning, and then subjecting a resulting active fraction to HPLC to purify the polypeptide through an adsorption, elution and fractioning.

The resulting polypeptide is disclosed in no literature, has an amino acid sequence of H—Ala—Thr—Cys—Asp—Leu—Leu—Ser—Gly—Thr—

Gly—Ile—Asn—His—Ser—Ala—Cys—Ala—Ala—His—

Cys—Leu—Leu—Arg—Gly—Asn—Arg—Gly—Gly—Tyr—

Cys—Asn—Gly—Lys—Ala—Val—Cys—Val—Cys—

Arg—Asn and shows not only an antibacterial but also an anti-virus activity.

Therefore, the present invention also intends to such novel polypeptide per se and use thereof as an antibacterial or anti-virus agent.

According to the method of the invention, such useful polypeptide can be obtained in a large amount by merely enlarging a scale for the cultivation of the cell line.

The polypeptide according to the invention is excellent in thermal stability, as apparent from that the method comprises the thermal treatment, which means that it is useful as an antibiotic additive for foodstuffs and more particularly for those requiring a thermal processing.

The polypeptide shows almost no toxicity, similar to those as already obtained by the present inventor.

In case of preparing a drug with use of the polypeptide as an effective ingredient, there is no limitation in form thereof and thus the drug may be made into various forms for oral or none-oral administration. As a dosage for therapeutic purpose, it is preferable to give on the basis of the polypeptide in a range of 1 to 500 mg/day, for instance 5 mg/day for an adult.

DETAILED DESCRIPTION OF THE PREFERRED EMBODIMENT

Figure 1:
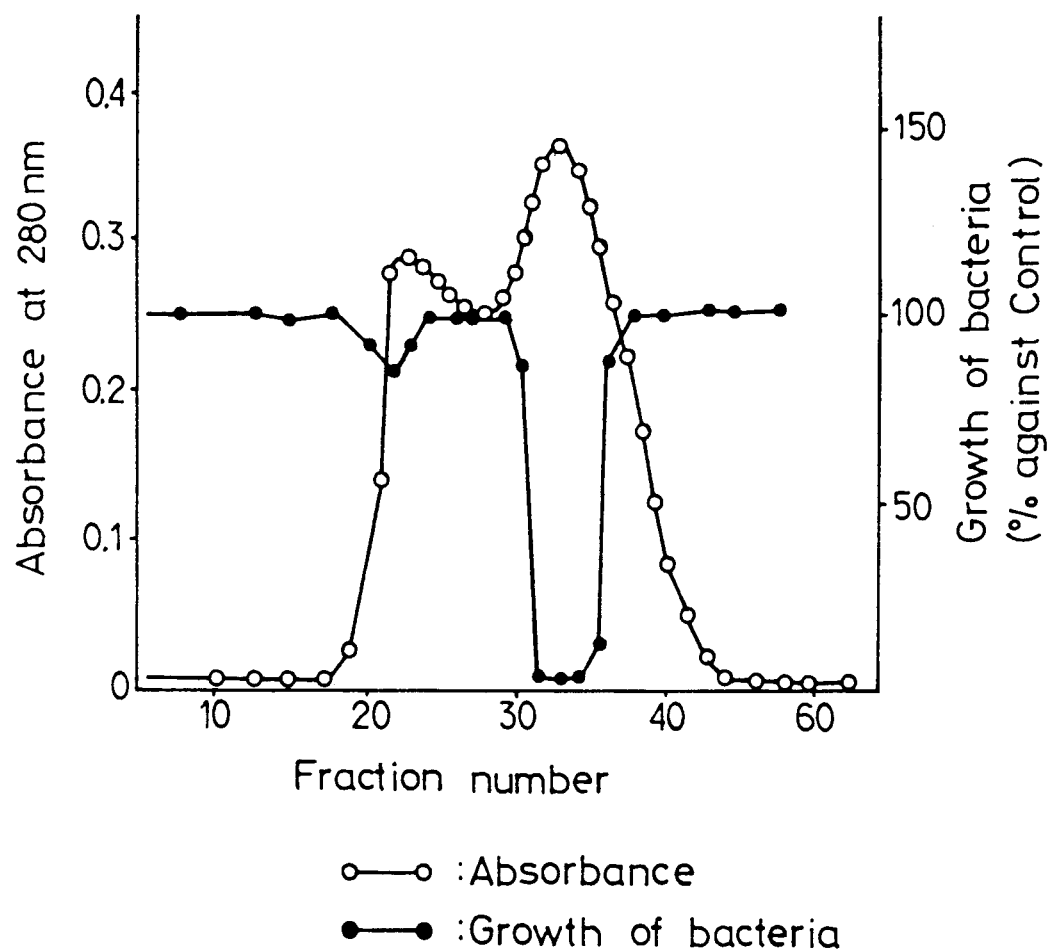
FIG. 1 is a chromatogram showing an elution pattern on a biologically active polypeptide according to the invention, when Sephadex G-50 column is employed in after heat treating, to obtain the same.

The invention will now be further explained with reference to an Example for obtaining a biologically active polypeptide, Pharmacological Test Example as well as Medicine Preparation Example.

EXAMPLE (a) Cultivation of cell

In a sterilized culture medium proposed by Mitsuhasi et al (sodium chloride 7 g/l, potassium chloride 0.2 g/l, calcium chloride dihydrate 0.2 g/l, magnesium chloride hexahydrate 0.1 g/l, sodium hydrogen phosphate monohydrate 0.2 g/l, sodium hydrogen carbonate 0.12 g/l, glucose 4 g/l, lactoalbuminhydrolysate 6.5 g/l and yeastlate 5.0 g/l; pH 6.5), cells established from Sarcopharga peregrina embryo (the cells being named as —NIH Sape-4 cell—) were inoculated in an amount of $1 \times 10^6$ cells/ml of the culture medium, and cultivated at 25° C. for 7 to 10 days. A passage was done, when the number of cells reached about $2 \times 10^7$ cells/ml of the medium and the medium was recovered through a centrifugal treatment.

(b) Separation and purification of an antibacterial polypeptide

In 500 ml of the culture medium obtained by the procedure described in said Item (a), 1500 ml of 10 mM-phosphate buffer (pH 6.0) were added to control the pH and salt concentration of the medium. The resulting solution was applied to a carboxymethylcellulose column (3.4×20.0 cm) which was then washed with a fresh buffer solution identical to the above.

To the column 520 mM-NaCl containing phosphate buffer was passed to collect each fraction by 5 ml. An absorbance at 280 nm, an antibacterial activity according to the method by OKADA et al and using an Escherichia coli (K12 594 strain) ["Biochem. J." Vol. 211, pages 724 to 734 (1983)] as well as absorbance at 650 nm were measured on each fraction to identify fraction(s) having antibacterial activity.

The antibacterial fractions were combined and heated at 100° C. for 10 minutes and then centrifugally treated to remove a precipitate formed therein. The resulting supernatant was concentrated by ultrafiltration. The concentrate was treated with Sephadex G-50 column (1.5×60.0 cm) and an eluate was fractionated by each 2 ml to determine an absorbance at 280 nm and antibacterial activity, in the manner similar to the above. In this case, 130 mM-NaCl containing phosphate buffer (pH 6.0) was employed for elution. Results are shown in FIG. 1.

Figure 2:
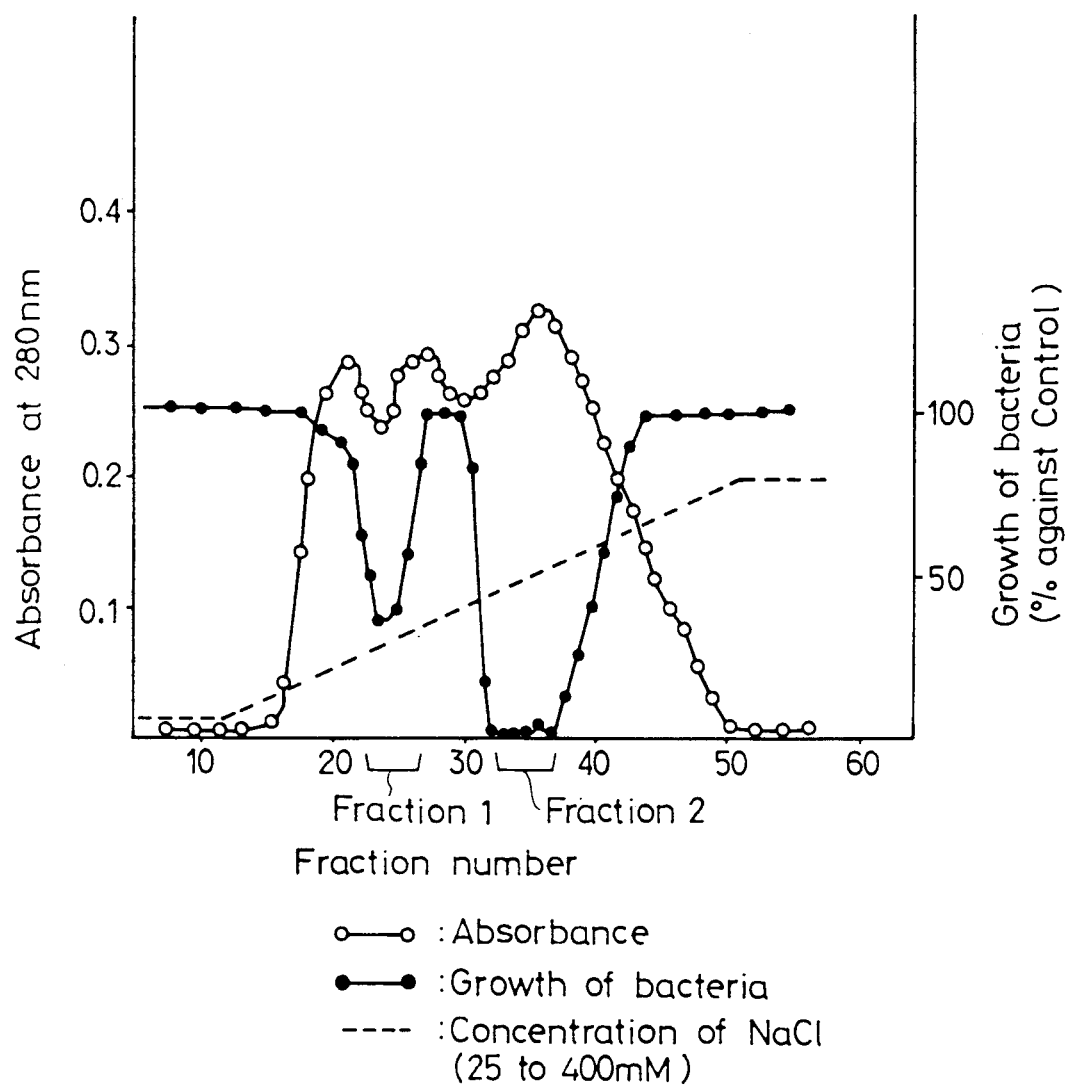
FIG. 2 is a chromatogram similar to that of FIG. 1 but in the second stage using CM-cellulose column.

The antibacterial fractions apparent from the Figure were combined and diluted with use of 10 mM-phosphate buffer to increase its volume 5 times. The resulting solution was subjected to carboxymethylcellulose column (2.0×4.0 cm) and an adsorptive was eluted with a linear gradient method using 25 mM to 400 mM-NaCl containing phosphate buffer. An absorbance at 280 nm and antibacterial activity of the eluate were measured as the above manner to obtain results shown in FIG. 2.

Figure 3:
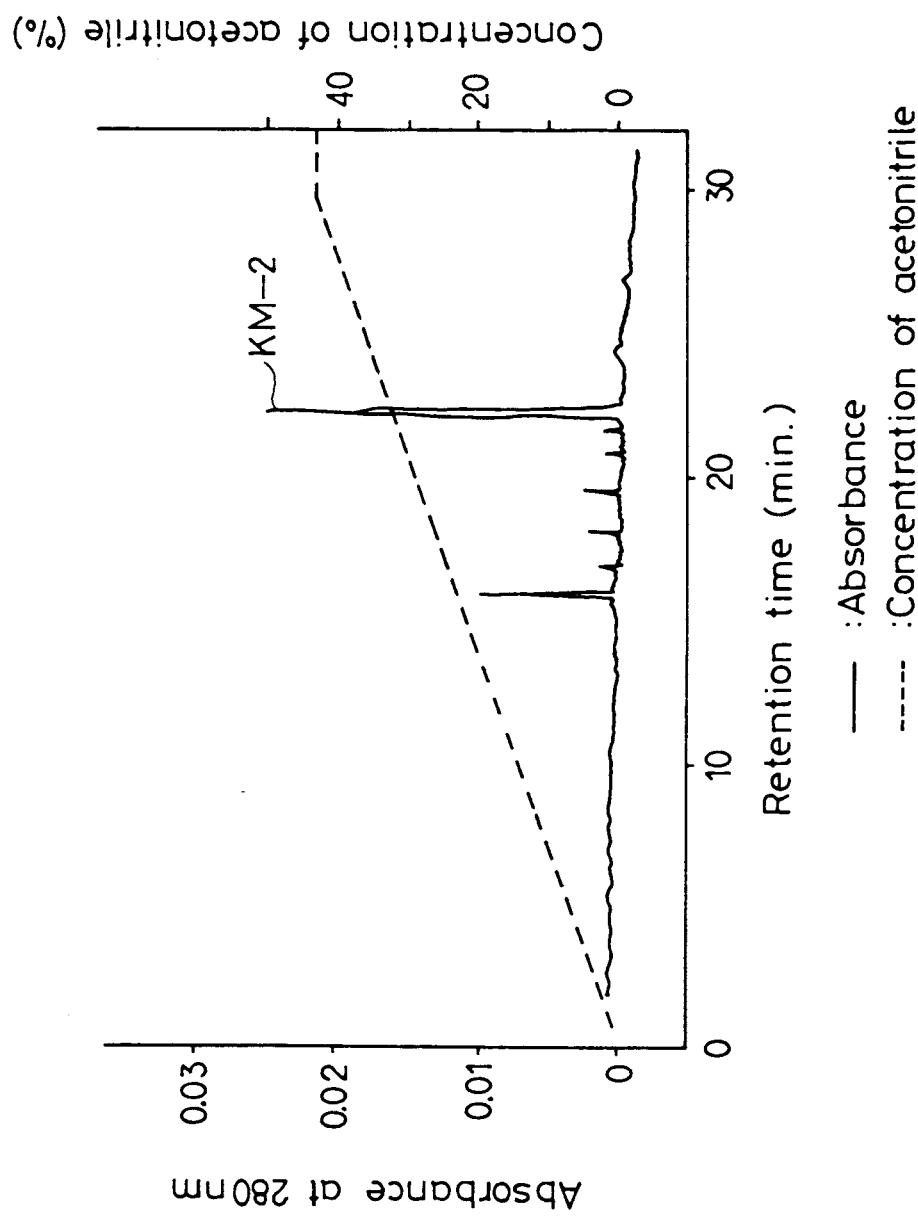
FIG. 3 is chromatogram similar to those in FIGS. 1 and 2 but in the final third stage of reverse phase HPLC.

Among the antibacterial fractions 1 and 2 apparent from the Figure, the former fractions were combined and fractionated with a reverse phase HPLC (Synchropack RPP-C18 column) to obtain results shown in FIG. 3.

The fractions corresponding to the main peak in the Figure were obtained to afford the desired biologically active polypeptide which was named as —KM-2—.

Followings are the conditions for the reverse phase HPLC.
Reagent A: 0.05% Trifluoroacetate/water,
Reagent B: 0.05% Trifluoroacetate/99% Acetonitrile,
Gradient: Linear gradient with use of 5% Reagent B in
Reagent A and 43% Reagent B in Reagent A,
Flow velocity: 2 ml/min.

(c) Determination of amino acid sequence for KM-2

An amino acid sequence for KM-2 was checked with use of a gas-phase protein sequencer (Type 470A Protein Sequencer marketed by Applied Biosystems Inc.) to determine the same as follows.

H—Ala—Thr—Cys—Asp—Leu—Leu—Ser—Gly—Thr—

Gly—Ile—Asn—His—Ser—Ala—Cys—Ala—Ala—His—

Cys—Leu—Leu—Arg—Gly—Asn—Arg—Gly—Gly—Tyr—

Cys—Asn—Gly—Lys—Ala—Val—Cys—Val—Cys—

-continued

Arg—Asn

PHARMACOLOGICAL TEST EXAMPLE (Measurement of anti-virus activity)

Figure 4:
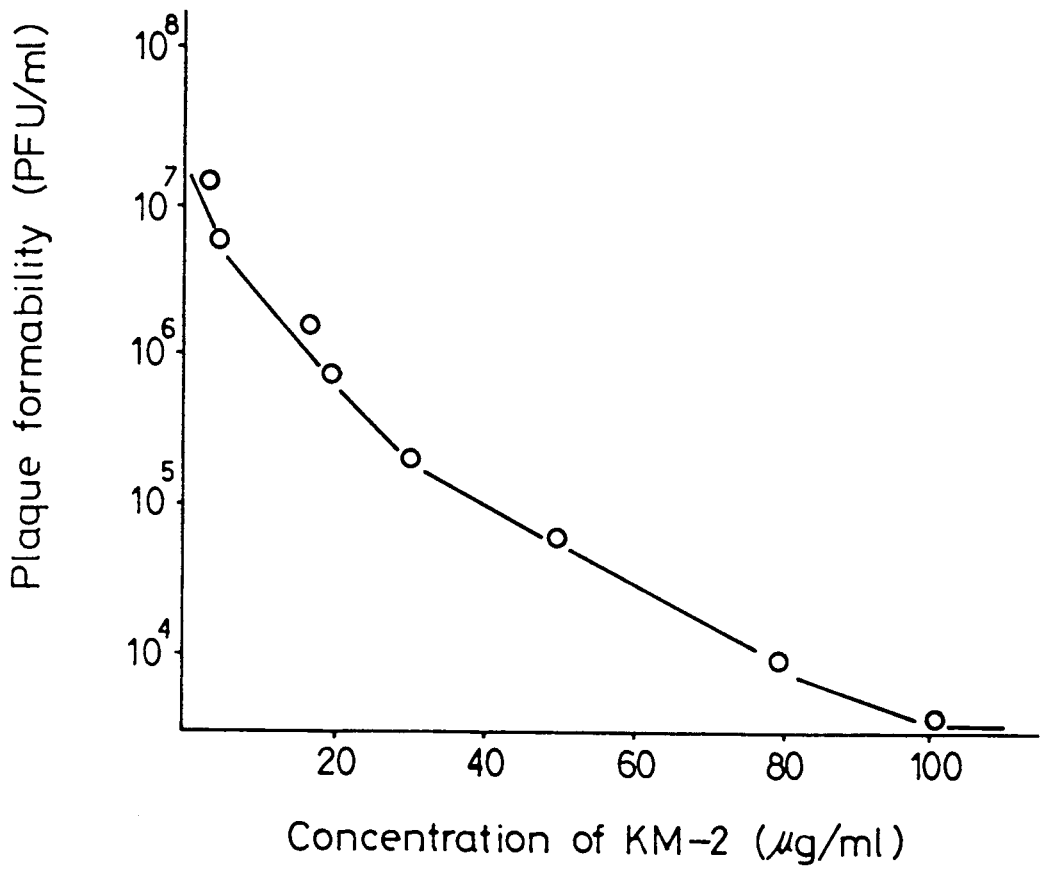
FIG. 4 is a graph showing an anti-virus activity of the polypeptide.

A direct neutralizing activity of KM-2 to herpes simple virus was measured in accordance with a method as by Lehrer ["J. Virology" Vol. 54, pages 467–472 (1985)] to obtain results shown in FIG. 4.

It can be seen from the Figure that a plaque formability due to the virus is directly inhibited.

MEDICINE PREPARATION EXAMPLE (Dry powder for injection)

The biologically active polypeptide (KM-2) was sterilized in a conventional manner, aseptically charged the same into each vial by 5 mg, freeze dried to make the same into a dry powder and sealed the vial.

When using for injection, the dry powder is dissolved into saline, aqua pro injection or the like.

What is claimed is:

1. A purified antiviral active polypeptide having an amino acid sequence shown by the formula of H—Ala—Thr—Cys—Asp—Leu—Leu—Ser—Gly—

—Thr—Gly—Ile—Asn—His—Ser—Ala—Cys—Ala—

—Ala—His—Cys—Leu—Leu—Arg—Gly—Asn—Arg—

—Gly—Gly—Tyr—Cys—Asn—Gly—Lys—Ala—Val—

—Cys—Val—Cys—Arg—Asn.

2. An anti-virus agent which comprises a virucidal effective amount of a biologically active polypeptide having an amino acid sequence shown by the formula of H—Ala—Thr—Cys—Asp—Leu—Leu—Ser—Gly—Thr—

Gly—Ile—Asn—His—Ser—Ala—Cys—Ala—Ala—His—

Cys—Leu—Leu—Arg—Gly—Asn—Arg—Gly—Gly—Tyr—

Cys—Asn—Gly—Lys—Ala—Val—Cys—Val—Cys—

Arg—Asn, and a pharmaceutically acceptable inert carrier for the popypeptide.

* * * * *